(12) United States Patent
Sentis et al.

(10) Patent No.: US 10,406,379 B2
(45) Date of Patent: Sep. 10, 2019

(54) PORTABLE RECHARGEABLE LED RED LIGHT CAVITY HEALING DEVICES

(71) Applicants: Nicole Kerstin Sentis, Santa Monica, CA (US); Adolfo Ribeiro, Venice, CA (US)

(72) Inventors: Nicole Kerstin Sentis, Santa Monica, CA (US); Adolfo Ribeiro, Venice, CA (US)

(*) Notice: Subject to any disclaimer, the term of this patent is extended or adjusted under 35 U.S.C. 154(b) by 202 days.

(21) Appl. No.: 15/455,770

(22) Filed: Mar. 10, 2017

(65) Prior Publication Data

US 2017/0333728 A1 Nov. 23, 2017

Related U.S. Application Data

(60) Provisional application No. 62/339,032, filed on May 19, 2016.

(51) Int. Cl.
*A61N 5/06* (2006.01)

(52) U.S. Cl.
CPC ......... *A61N 5/0603* (2013.01); *A61N 5/0613* (2013.01); *A61N 2005/063* (2013.01); *A61N 2005/0605* (2013.01); *A61N 2005/0606* (2013.01); *A61N 2005/0607* (2013.01); *A61N 2005/0608* (2013.01); *A61N 2005/0611* (2013.01); *A61N 2005/0626* (2013.01); *A61N 2005/0632* (2013.01);
(Continued)

(58) Field of Classification Search
CPC combination set(s) only.
See application file for complete search history.

(56) References Cited

U.S. PATENT DOCUMENTS 5,178,466 A 1/1993 Chiu
5,211,479 A 5/1993 Coffey
(Continued)

FOREIGN PATENT DOCUMENTS

CA 2675552 A1 2/2011
EP 2044973 A1 4/2009

OTHER PUBLICATIONS

Chaves et al., Effects of low-power light therapy on wound healing: Laser x LED, An Bras Dermatol. 2014; 89(4)616-23.
(Continued)

*Primary Examiner* — Scott Luan
(74) *Attorney, Agent, or Firm* — Trojan Law Offices (57) ABSTRACT

A light-emitting diode (LED) therapy device and method of use is provided that increases healing of tissues by targeting damaged tissue at a predetermined wavelength and pulsed at a predetermined frequency. The device includes a housing and a light radiation module enclosed within the housing. The light radiation module includes an LED, a controller unit connected to the LED to control wavelength and pulsed frequency of the LED, and a rechargeable power source. The device also includes a light-diffusing member connected to the housing designed to diffuse light emitted from the LED to damaged tissue in a human cavity. Light in the red or near infrared range and pulsed at a Nogier frequency increases the effectiveness of the LED device to stimulate healing of damaged tissues. Particular devices include incorporation into a pacifier for healing an infant's gums, or nasal, auditory, vaginal, or anal cavities and adults or children.

20 Claims, 8 Drawing Sheets

(52) U.S. Cl.
CPC .......... *A61N 2005/0645* (2013.01); *A61N 2005/0651* (2013.01); *A61N 2005/0659* (2013.01); *A61N 2005/0662* (2013.01)

(56) References Cited

U.S. PATENT DOCUMENTS

| | | | |
|---|---|---|---|
| 5,534,013 A | 7/1996 | Leindler | |
| 7,119,498 B2 | 10/2006 | Baldwin | |
| 2005/0015121 A1 | 1/2005 | Molina | |
| 2006/0167531 A1* | 7/2006 | Gertner | A61N 5/0603 607/86 |
| 2007/0233208 A1 | 10/2007 | Kurtz | |
| 2008/0033512 A1* | 2/2008 | Yu | A61N 5/0603 607/88 |
| 2009/0088824 A1 | 4/2009 | Baird | |
| 2009/0198275 A1* | 8/2009 | Godown | A61J 17/005 606/236 |
| 2010/0042188 A1* | 2/2010 | Nissila | A61N 5/0603 607/93 |
| 2011/0224584 A1* | 9/2011 | Pryor | A61H 21/00 601/15 |
| 2012/0209326 A1* | 8/2012 | Lutes | A61J 17/005 606/234 |
| 2014/0272770 A1* | 9/2014 | Hurley | A61C 19/063 433/29 |
| 2015/0231408 A1* | 8/2015 | Williams | A61N 5/06 607/88 |

OTHER PUBLICATIONS

Website; Red Light Therapy; https://redlighttherapy.lighttherapyoptions.com/red-infrared-light-wound-healing.
Mylighttherapy.com; Nogier Frequencies; http://www.mylighttherapy.com/nogier-frequencies.html, Nogier Frequencies.
Wheelan et al., Effect of Light-emitting Diode Irradiation on Wound Healing; J Clin Laser Med Surg. Dec. 2001;19(6):305-314).
Kim et al., Is Light-Emitting Diode Phototherapy (LED-LLLT) Really Effective? Laser Therapy 20.3:205-215.
Nogier Frequency Information; http://www.diomedics.com/nogierFrequencyGuide.php.
Your Complete Guide to Red Light Therapy; https://redlighttherapy.lighttherapyoptions.com/red-light-therapy/.
Ferraesi et al., Light-emitting diode therapy in exercise-trained mice increases muscle performance, Cytochrome C oxidase activity, ATP and cell proliferation, Ferraesi et al., J Biophotonics. Sep. 2016;9(9):976).
Bashkatov et al., Optical Properties of Skin, Subcutaneous, and Muscle Tissues: A Review, J. Innovative Opt. Health Sci., vol. 4, No. 1 (2001) 9-38.
S.L. Jacques Corrigendum: Optical properties of biological tissues: a review, Phys. Med. Biol. (2013) 58 R37.

* cited by examiner

PORTABLE RECHARGEABLE LED RED LIGHT CAVITY HEALING DEVICES

CROSS-REFERENCE TO RELATED APPLICATIONS

This application claims priority to and benefit of U.S. Provisional Patent Application No. 62/339,032, filed May 19, 2016, the content of which is incorporated by reference in its entirety.

FIELD OF THE DISCLOSURE

The present invention relates to a healing device and method, and more particularly, to the use of red light to aid in wound healing.

BACKGROUND OF THE INVENTION

The use of light for healing has long been practiced. Specific light wavelengths have been used to treat various ailments and to stimulate the body's natural tissue healing abilities. Light emitting diodes (LEDs) that emit light in the red wavelength (around 630 nm-700 nm) have been shown to decrease pain, aid in wound healing, and increase skin rejuvenation.

The mechanism of how red light therapy aids in tissue healing is not completely understood, but red light has been shown to increase release of ATP, an important source of energy, which thereby aids in activity performance. (See "Light-emitting diode therapy in exercise-trained mice increases muscle performance, Cytochrome C oxidase activity, ATP and cell proliferation," Ferraesi et al., J Biophotonics. 2016 September; 9(9):976). Light, especially light in the red and near-infrared range has been shown to have the ability to penetrate skin layers and energize fibroblast cells to produce collagen and elastin, which helps repair skin damage. LED light therapy has also been shown to increase growth of epithelial cells, improve recovery of musculoskeletal training injuries, and reduce pain in children suffering from oral mucositis. (See "Effect of NASA Light-Emitting Diode Irradiation on Wound Healing," Whelan HT, J Clin Laser Med Surg. 2001 December; 19(6):305-314). Animal studies have shown that LED light therapy increases cell growth in mouse-derived fibroblasts, rat-derived osteoblasts, rat-derived skeletal muscle cells and also has the ability to decrease wound size. Id.

Most devices that use LEDs for healing, such as the device disclosed European Pat. App. Pub. No. EP2044973A1 to Vibor, are based on using a matrix of LEDs on a matrix board. These types of devices are similar to tanning beds, except instead of UV lamps within the bed, the lamps are replaced with red LEDs. Although the large bed devices are useful for treating certain types of tissue damage, they are bulky and expensive. They also require the user to dedicate several hours per week in order to receive a sufficient amount of light to observe positive effects.

In additional to LED beds, other types of devices have been used to aid in body repair. Light therapy bandages have been used to treat wounds, such as the one disclosed in U.S. Patent Pub. No. 20070233208A1 to Kurtz et al. Bandage devices such as these are most effective for topical wounds. Other devices, such U.S. Patent Pub. No. 20090088824A1 to Baird et al. uses a handheld wand-like device for LED based phototherapy to rejuvenate cells.

In addition to devices that stream a constant light source to a wounded area, therapy devices also exist that pulse light to treat wounds, such as the wand device disclosed in U.S. Patent Pub. No. 20050015121A1 to Molina, which uses pulsed light having a wavelength between 600 nm to about 980 nm, well into the infra-red range. While these devices may be effective to treat certain types of wounds in specific areas of the body, there remains a need for light therapy devices that are easy to use, inexpensive to manufacture and can effectively treat wounds that have traditionally been difficult to expose to light.

BRIEF SUMMARY OF THE PRESENT INVENTION

The present invention provides for devices that are portable, rechargeable, and use light emitted from diodes in the range of 600-700 nm in order to speed the wound healing process and decrease pain associated with wounds. The devices are especially useful for treating wounds in the oral, aural, nasal, vaginal, and anal cavities of a person. These wound areas have traditionally been difficult to treat using light therapy because light from hand-held and light bed devices cannot penetrate body cavities well.

Advantages of the present invention over other types of wound therapy, including light therapy and traditional wound healing methods, are that the devices of the present invention are drug-free, wearable, cordless, made of germ resistant materials, and have the capability of connecting wirelessly with mobile devices, and can diffuse light to treat tissue within a large area of the cavity.

In one embodiment the LED therapy device includes a housing and light radiation module substantially enclosed within the housing. The light radiation module includes an LED for emitting light at a predetermined wavelength, a power source electrically connected to the LED, and a controller unit connecting the power source and LED. The controller unit is capable of controlling pulse frequency of the LED at a predetermined frequency. The device also includes a light-diffusing member connecting to the housing. The light-diffusing member is designed to diffuse and project light emitted from LED to a wide area of tissue located within the cavity.

In one aspect of the invention, the LED wavelength of light is between 600 and 700 nm, and the light is pulsed at a Nogier frequency (292 Hz), or a harmonic of the Nogier frequency (i.e. 584 Hz, 1168 Hz, 2238 Hz, etc.). Light pulsed at the Nogier frequency or harmonic of the Nogier frequency increases the tissue repair rate compared to the tissue repair rate of tissue treated by light not pulsed at the Nogier frequency.

Embodiments of the invention can take many forms to fit within specific cavities. In one aspect, the embodiment is in the form of an infant pacifier. This form is advantageous for healing the gums or other legions within the mouth of an infant. This embodiment is especially useful for when the infant is teething. In this embodiment, the light-diffusing member is a flexible nipple made from silicone or other flexible elastomeric material. When the infant places the pacifier in his or her mouth, light from the LED diffuses through the nipple and illuminates the entire oral cavity, including the gums. This device is more effective at treating gum wounds than a hand-held light therapy device, or a light therapy bed, because a silicone nipple within the mouth is better capable of diffusing light throughout the entirety of the oral cavity than a hand-held wand or light therapy bed.

The silicone nipple is designed in order to maximize the internal reflection of the light and to be an optical light guide that directs the LED red light toward the front gums and the back gums of an infant. In one embodiment, there is a single LED covered by a light pipe that directs the light into a wide angle increase the light coverage of the front and back gums of an infant. The light pipe also has the mechanical function of holding the silicone nipple in place to prevent detachment during intense suction.

In another aspect of the invention, the device is configured for particular use in the ear. The housing includes an optical guide for directing light through the housing. The optical guide is characterized as having an elongated tubular region with a first end that is in proximity to the LED and a second end opposing the first end. The light-diffusing member is a removable flexible silicone cap designed to attach to the second end of the elongated tubular region and project light into and throughout the ear canal, which fitting firmly within one end of the ear canal.

In yet another aspect of the invention, the device is configured to fit into the nostrils of human. Each nostril is fitted with a separate nostril LED device connected together with a bridging member so that there are two devices connected to each other by the bridging member. The optical guide of the first device and the optical guide of the second device are spaced between 1 and 3 centimeters from each other and designed to fit within two nostrils of a human. Light emanating from the first and second devices is directed to a nasal cavity of a human.

In yet another aspect of the invention, the device is configured to fit within the vaginal cavity or anal cavity of a person to aid in repair of vaginal or anal tissue. The device is characterized as having an elongated body for insertion into anal or vaginal cavity. The housing along the elongated body is a transparent or translucent shell, preferably made silicone rubber or other elastomeric composition. The housing encloses an optical guide for placement of a plurality of LEDs along the longitudinal axis of the device. The optical guide is connected to a compartment enclosing a rechargeable power source. Optionally covering this embodiment is elastomeric tubular sheath, such as a condom or other type of latex sheath, designed to fit over the elongated housing and generally conform to the shape of the elongated housing. The condom acts as a protective layer between the device and user. The condom may be coated with a lubricant to aid in smooth insertion into the cavity. The lubricant may comprise a lotion or ointment that further aids in tissue repair such as ointments having active ingredients of petrolatum and key ingredients of mineral oils, ceresin, lanolin, glycerine, panthenol, vitamin B, and bisabolol. The combination of the translucent elongated housing, elastomeric sheet, and ointment aid in light dispersion so that a greater amount of tissue can be exposed to LED light when the device is inserted into the cavity.

In yet another embodiment of the invention, a method of promoting healing of tissues using red LEDs. The method includes inserting a device into an animal cavity, such as the mouth, ear canal, nostril, anal or vaginal cavity. The device includes a housing, a light radiation module substantially enclosed within the housing, an LED having at least one predetermined wavelength, a controller unit connected to the LED, the controller unit capable of controlling pulse frequency of the LED at least one predetermined frequency, a power source, and a light diffusing member connected to the housing. The method includes the step of illuminating the LED, preferably at a wavelength between 600 nm and 700 nm, and pulsing the LED at a Nogier frequency, such as at a frequency of 292 Hz, 584 Hz, or 1168 Hz.

DETAILED DESCRIPTION OF EMBODIMENTS

The invention now will be described more fully hereinafter with reference to the accompanying drawings, in which embodiments of the invention are shown. This invention may however be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," "upper" or "top," "left" or "right," "above" or "below," "front" or "rear," may be used herein to describe one element's relationship to another element as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. The invention illustratively disclosed herein suitably may be practiced in the absence of any elements that are not specifically disclosed herein.

Turning to the various embodiments, all embodiments can be used to aid in healing wounds, irritation or infections in human cavities. The embodiments use an electrically rechargeable power source and at least one LED light in the range of about 630 nm to 700 nm (red and near infrared), which has been shown to stimulate wound healing and decrease pain associated with wounds. Light outside this range, from 600 nm to 980 nm has also been shown to have positive effects because body tissue can absorb light having wavelengths in this range. In preferred embodiments, the LED light is in the range of 660 nm to 680 nm. Light having wavelength in this range has the ability to penetrate layers of skin (up to around 2 mm-7 mm) and energize fibroblast cells that produce collagen and elastin, thereby helping repair damaged tissue. Embodiments allow users to wear the device during the day and night, profiting from the healing effects of red light without dedicating long hours under fixed lamps or inside LED light beds. As light therapy efficiency depends on the exposure time, light therapy approaches using these devices will yield faster and better effects by being used for several hours per day instead of several sessions of just a few hours per week or per month.

Embodiments of the present invention are advantageous over other light therapies because the present embodiments are specifically designed to target wounds inside of cavities (oral, aural, nasal, vaginal and anal) and also employ the use of predetermined wavelengths and LED pulsing to stimulate wound healing. While proponents of light therapy devices claim that light therapy devices using lamps can reach internal areas of the human body by outside indirect exposure, these devices cannot be as effective as directly applying light using device specifically designed to be inserted into a cavity having damaged tissue.

Embodiments are made of medical grade plastic and enclose a light radiation module that controls an LED to emit wavelengths in the visible red spectrum and near infrared. The light is optically directed inside human cavities via clear buffer, for example, a transparent or translucent silicone that is part of the device. To increase the healing effects, emitted light is pulsed at "Nogier frequencies," also known as the cellular frequency. Nogier frequencies are frequencies in multiples and factors of 292 Hz (e.g. 73 Hz, 146 Hz, 584 Hz, 1,168 Hz, 2,236 Hz, 4,672 Hz, which are harmonics and factors of the Nogier frequency because these frequency can be attained by doubling 292 Hz or halving 292 Hz one or more times). Light emitted at these frequencies aid in repairing damaged tissue and increase healing process. Deviations of these frequencies from −30% to +30% have also been used to aid in healing and may be employed to repair damaged tissue.

FIGS. 1-4 illustrate embodiments designed as a pacifier 10 for an infant. Pacifiers utilizing lights are known, including U.S. Patent App. Pub. 20120209326A1 to Lutes et al., hereby incorporated for all purposes by reference in its entirety. In the present embodiment, FIGS. 1-4 includes a housing 36, a light radiation module 16 that controls output of one or more LEDs 2, and a light-diffusing member 18. In the embodiment shown FIGS. 1-4, the light-diffusing member 18 is a nipple and preferable is made from 100% food grade silicone and designed to maximize the contact with an infant's gums, and maximize light diffusion into the oral cavity. The pacifier 10 includes a handle 52 for the infant to hold and a mouth shield 50 to prevent the infant from inserting the pacifier 10 entirely into the oral cavity. The nipple 18 has a top region 28, middle region 32, and bottom region 30. The nipple 18 includes an outer surface 24 and an inner surface 26 that encloses a nipple cavity 34. The surfaces 24, 26 of the nipple 18 allow internal reflections of light emanating from an LED 2 to expose diffused radiated light throughout the entirety of the oral cavity. The light radiation module 16 comprises controller circuitry for at least one LED 2. LED controller circuitry that can control intensity, pulse, and wavelength of light have previously been disclosed, such as the controller circuitry disclosed in U.S. Pat. No. 7,119,498 to Baldwin et al., fully incorporated by reference in its entirety. LEDs may be those commonly used in the art. In one embodiment the LEDs are type 5 mm 3.5V, and are capable of emitting light between 660 nm and 680 nm. The LEDs 2 are disposed on or near the surface of light radiation module 16 and may be a single LED or a plurality of LEDs within the housing 36. The light radiation module 16 is preferable between 1 cm to 2 cm in width, but may be of any width that can fit within a waterproof compartment 56 surrounded by the housing 36 near the base 6 of the pacifier 10.

The light radiation module 16 and LEDs 2 connected to the module 16 are powered by a power source 14 such as a battery. A preferable power source is a rechargeable button cell lithium battery type cr2032. The control circuitry can pulse the LEDs 2 at or near the Nogier frequency of 292 Hz. The LED can also pulse at harmonic frequencies at or near Nogier frequency, such as at 584 Hz and 1168 Hz. The light radiation module 16 can also be wirelessly controlled by though variety of means, including using Bluetooth technology using such as Bluetooth Module a2dpC. The power source 14 can be charged by Qi wireless charger technology using an active coil (located inside a charging base) and a passive coil located in the electronic compartment of the pacifier. Various wireless charging technologies are well known and different types wireless chargers may be used without department from the spirit invention. The charging base can also have an ultraviolet light integrated in the top central part of base to sterilize the pacifier while it is charging. Bluetooth components may connect wirelessly to a controller, such as an app on a smart phone to control the output of the LEDs. The variables that the controller may be able to affect include intensity, pulse frequency, and wavelength.

Light emitted from the LED 2 can be controlled through a variety of means. The LEDs 2 can be turned on or off via the use of a power button or press switch 60. The press switch 60 is connected to a conductive member 98 (see FIG. 4) that is in electrical contact with the power source 14 and circuitry on the light radiation module 16 so that by pressing the power button 60, the LED can selectively be turned on or off. Preferably, the press switch 60 should require an amount of force that an adult can impart, but not an infant, so that an infant could not accidentally actuate the switch. An adult force press switch 60 prevents unnecessary battery drain by reducing the chances that an infant could turn the LEDs on when not in use. To prevent accidental turning on or off of the LED 2 by an infant, the device may employ multiple press switches that must be depressed simultaneously in order to turn on or off the device. An infant is unlikely to accidentally depress multiple press switches simultaneously on the pacifier so this ensures that only an adult would likely turn the device on or off.

A safety feature that prevents the user from accidentally directing light into the eyes is a light sensor 58 that activates the LEDs 2 only when the sensor 58 is exposed to sufficient light emitted from the LEDs 2. When the LEDs 2 are on and the pacifier 10 placed inside the infant's mouth, the sensor 58 would measure a high amount of light due to the reflection of the red light inside the infant's mouth back to the sensor 58. However, if the pacifier 10 is outside of the infant's mouth, the sensor 58 would measure a drop of light intensity, and turn the LEDs 2 off automatically. This sensor feature serves a double function, as it will prevent the infant from receiving directly light into the eyes should the pacifier 10 be removed or fall out of the infant's mouth, and it also saves batteries. Other types of sensors that detect the placement of an object in a mouth can also be used and incorporated into the present device, such as those disclosed in U.S. Patent App. Pub. 20090198275A1 to Godown et al.

Figure 4:
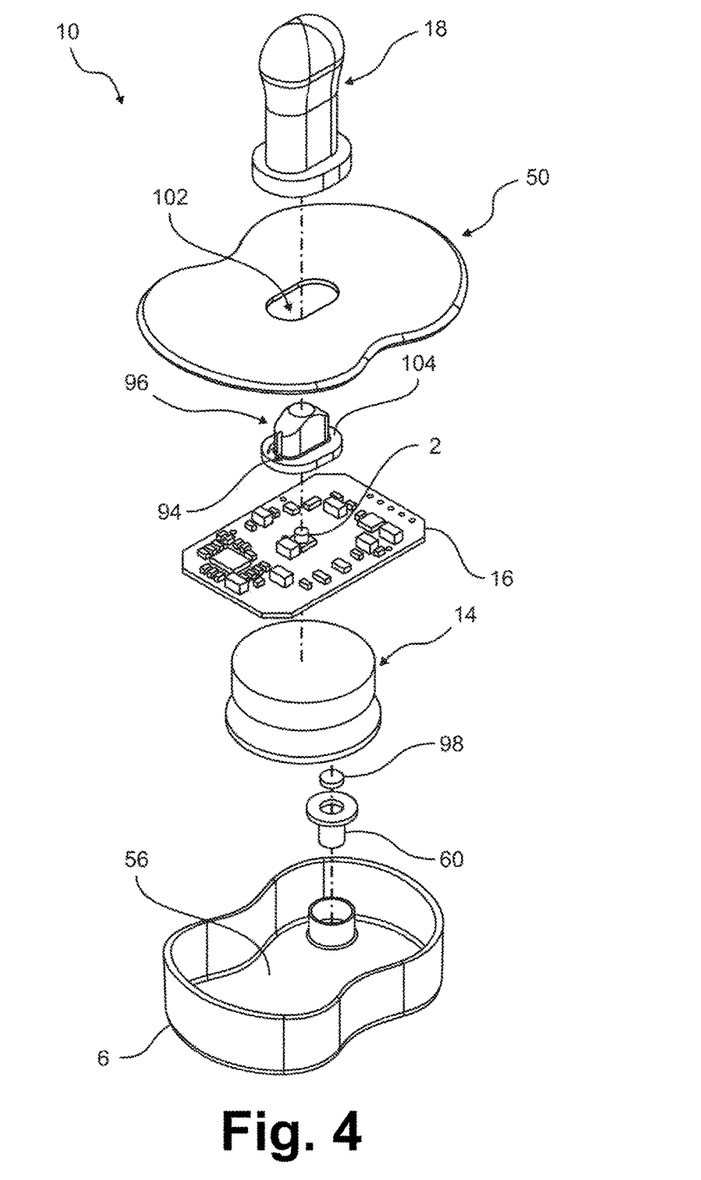
FIG. 4 is an exploded view of another pacifier embodiment, the embodiment having a light pipe to guide and disperse light from the LED to the front and back gums of the mouth of an infant.

An alternative pacifier embodiment is shown in FIG. 4 in an exploded view. A single LED 2 is positioned within the nipple 18 and further comprises a light pipe 96 that is positioned on top of, and surrounds, the LED 2. Although a single LED 2 is shown, multiple LEDs could be placed within the light pipe 96. The light pipe 96 serves a dual function. First, it spreads the emitted light to a wider angle, which better expose the gums of an infant to light. Second, it mechanically holds the silicone nipple 18 to the other components of the pacifier 10 thereby preventing detachment of the nipple during intense suction. As FIG. 4 illustrates, the top of light pipe 96 fits through an aperture 100 of the mouth shield 50. The base 104 of the light pipe 96 fits over the LED 2 and is below the mouth shield 50. Since the base 104 of the light pipe 96 is wider than the aperture 100 in the mouth shield, the light pipe 96 remains securely in place. The top 102 of the light pipe 96 is sized and shaped to securely fit within the interior cavity of the nipple and the light pipe 96 is press fit to attach to the nipple 18.

To account for the change of pressure inside the nipple 18 that occurs when an infant bites or sucks the nipple 18, the light pipe 96 can include an aperture 94 to balance the air pressure inside the nipple 18 with the air pressure of the compartment 56 housing the electrical components. Having an aperture that connects the nipple cavity with the housing 56, balances the air pressure within the device 10.

The light pipe 96 can have various features that increase the effectiveness of distributing light within the nipple 18 to target an infant's gums. The light pipe 96 can have guide walls that extend from a perimeter of the LED 2 to directly light upwards. When the light passes the guide walls, the dome shaped top 102 of the light pipe 96 can angle the light in various directions to ensure that light is being distributed at a wide angle within the nipple so that the light not only is directed to the tip of the nipple, but along the sides of the nipple as well.

The dimensions of the pacifier 10 shown in FIGS. 1-4 can be of a variety of shapes and sizes. One embodiment about 1.75 inches (4.5 cm) in length, about 2 inches (5 cm) in height and about 2 inches (5 cm) in depth.

Methods to effectively heal tissue involve exposure of damaged tissue to red light having at least a minimum threshold intensity for at least a minimum threshold time. Factors that influence the gum healing effects by the light include distance that the gums are away from the light source and the exponential decay of light as it penetrates the gum tissue. In one embodiment, the light irradiance is approximately 70 mW/cm$^2$. As the distance from the light source to the gums increase, the irradiance decreases significantly. For example, when the gums of the infant are approximately two centimeters (one inch) from the nipple of the pacifier, the light irradiance of a light source of 660 nm in mucous tissues decreases to approximately 10 mW/cm$^2$. (See Bashkatov et al., "Optical Properties of Skin, Subcutaneous, and Muscle Tissues: A Review, J. Innovative Opt. Health Sci., Vol. 4, No. 1 (2001) 9-38; and S. L. Jacques, Corrigendum: Optical properties of biological tissues: a review, Phys. Med. Biol. (2013) 58 R37. This irradiance is similar to the irradiance of a low level of sunlight. Since sunlight does not typically reach the gums of an infant the irradiance provided by pacifier is sufficient to reduce swelling and inflammation.

To achieve a median light irradiance of about 30 mW/cm$^2$ at about 1 mm inside the mucous gum tissue, a dosage of approximately 8 J/cm$^2$ provides enough light to develop new capillaries and allow a faster draining of lymphatic processes to increase gum healing. After inflammation decreases, it is typical the inflammation recurs after approximately 30 minutes. Therefore, in a preferred embodiment, light dosage can be delivered in the following manner. The light of the pacifier is turned on for approximately 2 minutes and 13 seconds at a value of 30 mW/cm$^2$, which equates to 4 J/cm$^2$. The pacifier is turned off for about 30 minutes and the pacifier is turned off (or removed from the infant's mouth) for approximately 30 minutes and the light is then turned on for another 2 minutes and 13 seconds to lead to a single dosage of 8 J/cm$^2$ per treatment. After one hour, the pacifier will turn off and should manually be turned on again to restart a sequence of dosage delivery. In a preferred embodiment, the pacifier should be used two to three times per day for the one-hour sequence.

In another embodiment, the can be activated between between one minute and three minutes, which provides either a higher dosage or lower dosage compared to the embodiment where the light is on for two minutes and 13 seconds. A decreased dosage based on a decreased amount of time of exposure may not sufficiently activate gum healing, and a higher dosage on time, not only could have a diminishing returns effect, but may decrease healing time to baseline healing time, comparable to no light therapy. In still further embodiments, the treatment sessions can be in 15 minute, 30 minute, 45 minute or 60 minute intervals without detracting from the spirit of the invention.

Figure 1:
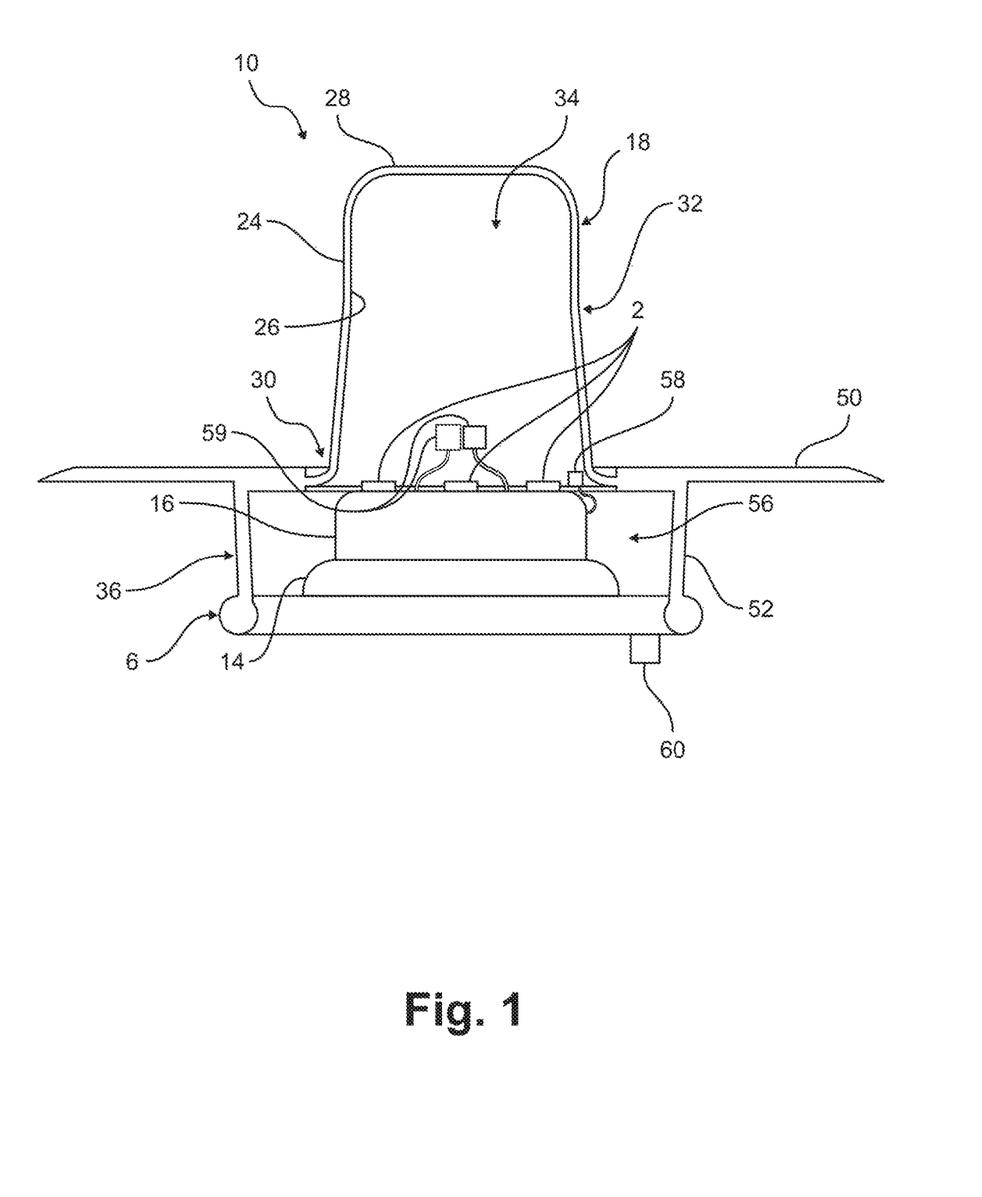
FIG. 1 is a cross sectional view of a pacifier embodiment of the device designed for use in the oral cavity of an infant.
Figure 2:
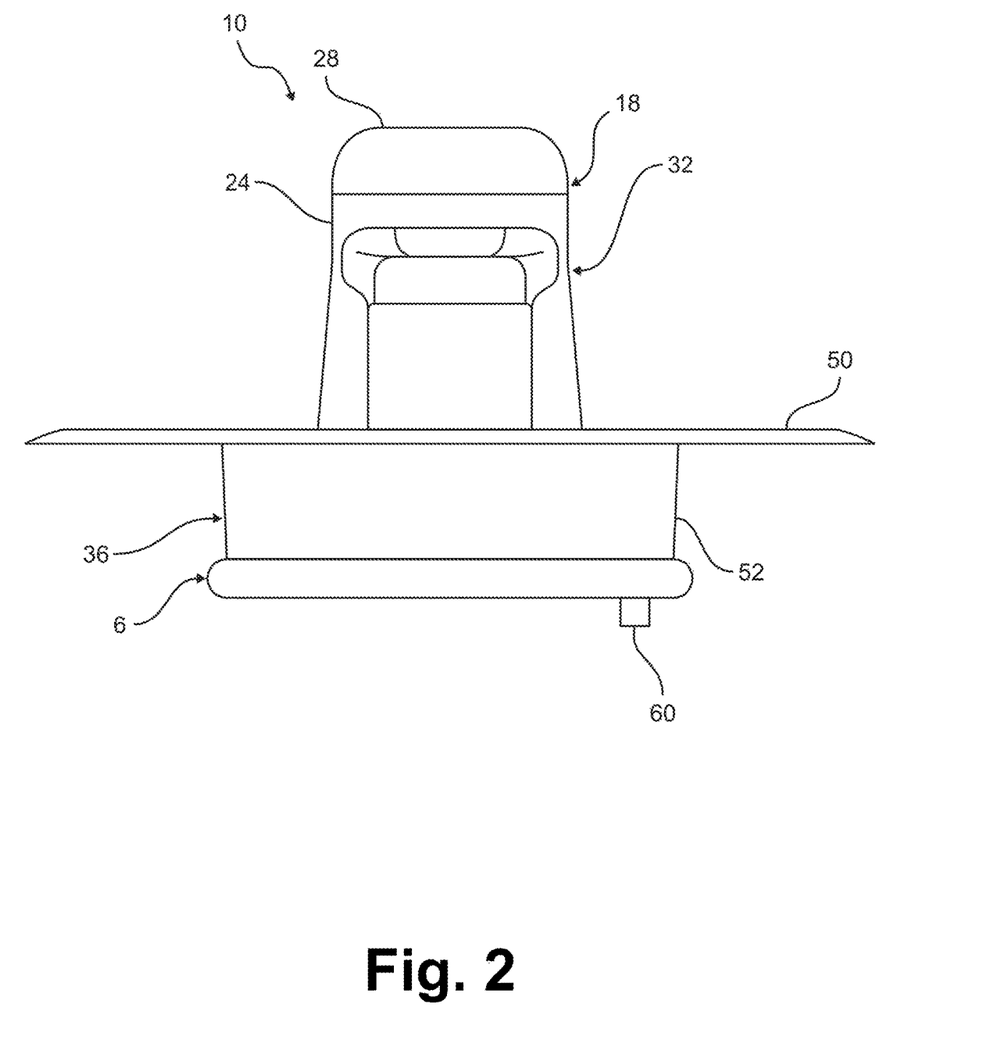
FIG. 2 is a side view of the embodiment of FIG. 1.
Figure 3:
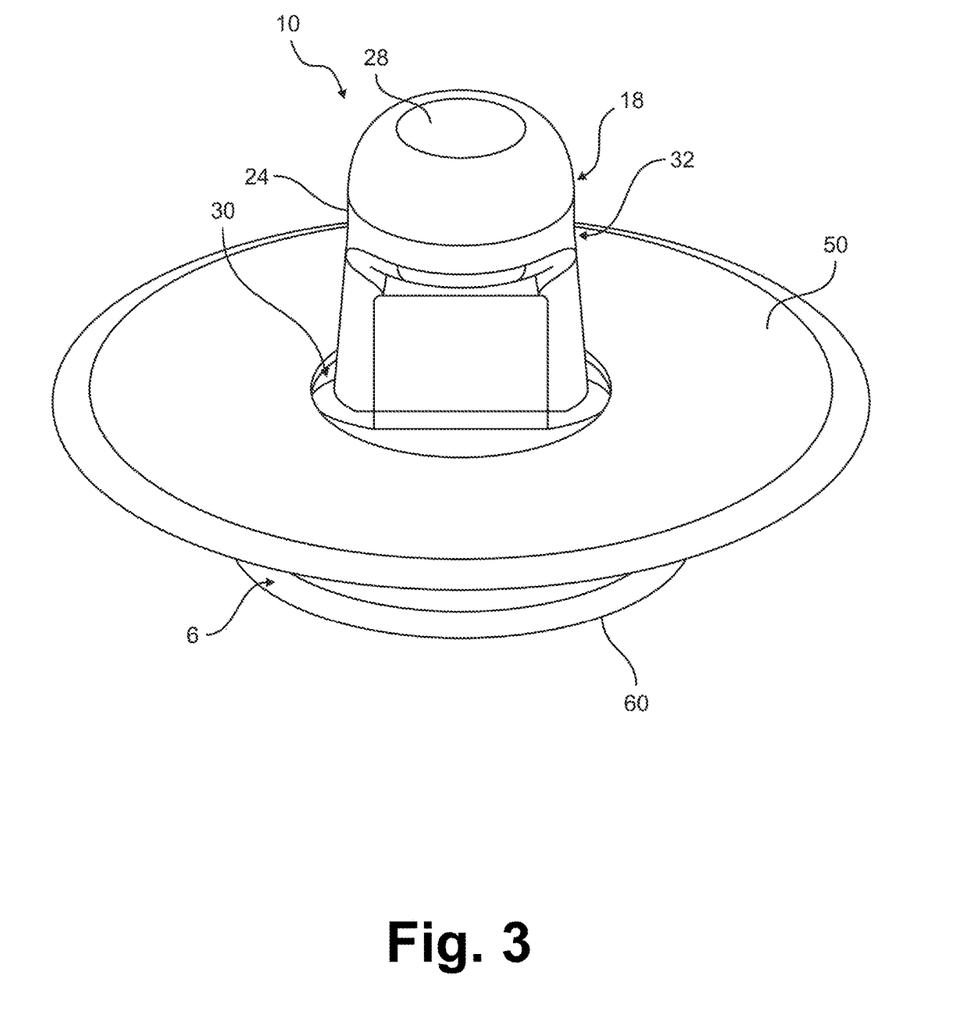
FIG. 3 is a perspective view of the pacifier embodiment of FIGS. 1 and 2.

In another embodiment of the invention, the pacifier uses a smart light dosage delivery. Instead of the light source being controlled by a timer, the light source is activated and deactivated being based on the temperature of the infant's gums. Inflammation of gums is associated with a temperature increase of the gums. The pacifier includes a thermocouple or temperature sensor 59 (as shown in FIG. 1) that is capable of measuring the temperature of the top and bottom gums. Pacifier thermometers are known in the art, such as those disclosed in U.S. Pat. No. 5,178,466 to Chiu, U.S. Pat. No. 5,211,479 to Coffey, and U.S. Pat. No. 5,534,013 to Zeindler, each incorporated by reference in their entireties. The pacifier monitors the gum temperature and delivers the appropriate dosage of light to reduce inflammation. As the temperature of the gums decreases due to reduction of inflammation, light source will deactivate. The circuitry 16 connected to the temperature sensor 59 monitors and temperature and controls activation and deactivation of the light source. FIG. 1 illustrates two temperature sensors 59, one disposed on the top side of the nipple and one disposed on the bottom side of the nipple, to each separately measure the temperature of the top and bottom gums, respectively.

Figure 5:
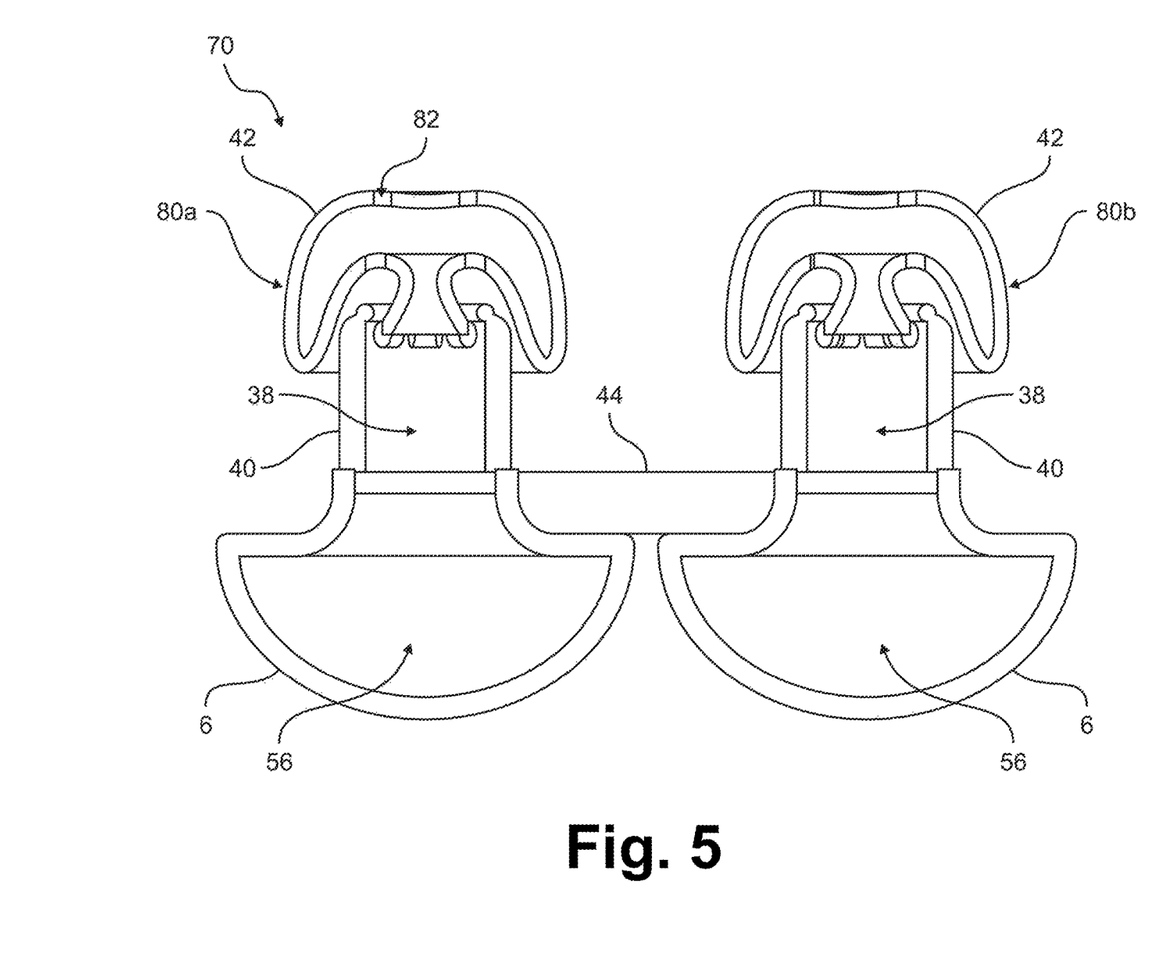
FIG. 5 is a cross sectional view of an embodiment of the device designed for use in the ear or nose of a person.
Figure 6:
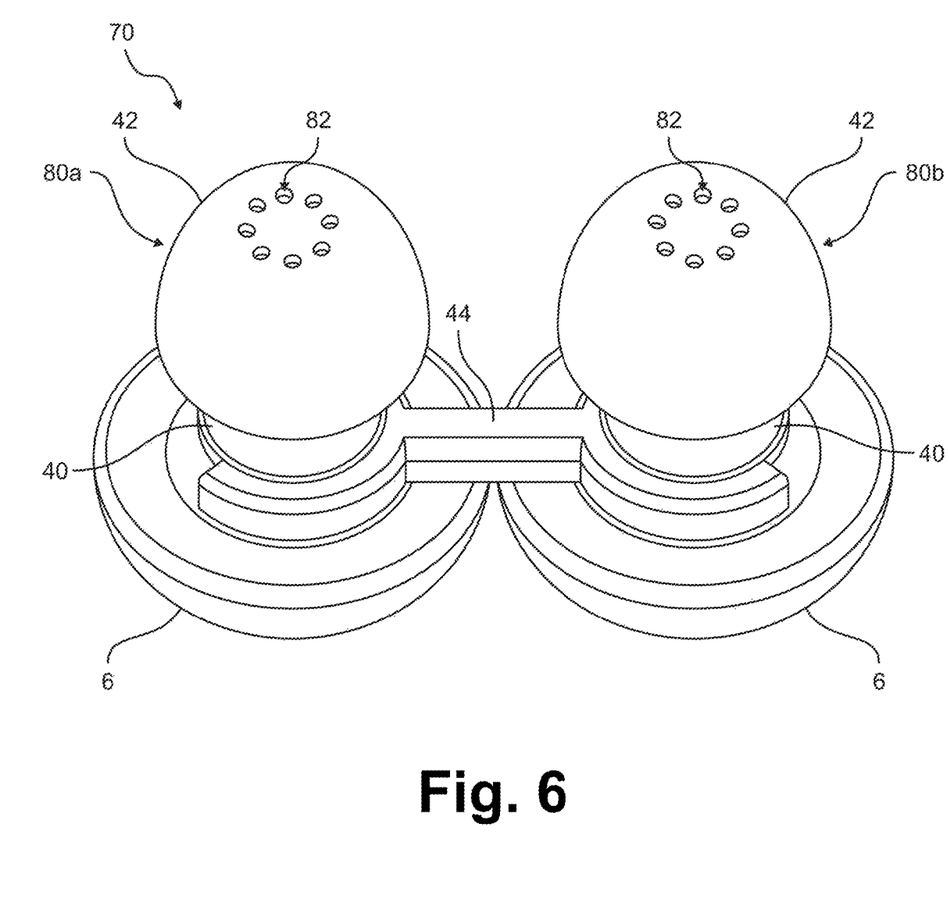
FIG. 6 is a top perspective view of the embodiment of FIG. 5.

FIGS. 5 and 6 illustrate an embodiment of an LED device designed to fit within the ear canal or nostrils of a person. The nostril LED device 70 comprises the same internal electrical components of the pacifier 10 shown in FIG. 1, including a light radiation module 16, LED 2, power source 14, and controller unit 16. The nostril LED device 70 is comprised of two individual devices 80a, 80b that can individually be used as ear LED devices. The individual ear devices 80a, 80b are connected by a bridge member 44. When the ear LED devices 80a, 8b are separated from the bridge member 44, the ear LED devices 80a, 80b are adapted to fit within the ear of a person. Modifications can be made to the nostril LED device 70 such that the bridge member 44 can permanently fix the ear devices 80a, 80b together.

The top of each ear LED device 80a, 80b has a flexible silicone cap 42 (or can also be made from other elastomeric compositions). The devices 80a, 80b can made in a variety of seizes to fit within the ear canal or nostril. The silicone cap 42 forms a flexible seal to hold the devices 80a, 80b within the ear, similar to how the silicone caps of ear bud headphones form a flexible seal to prevent ear bud headphones from falling out of the user's ears. The silicone cap 42 is preferably made from a breathable material and acoustically permeable material or have features, such as pores 82, that allow sound to travel through the ear LED devices 80a, 80b. The silicone cap 42 may also have a hollow center to allow light to project through the cap 42 onto the user's nasal tissue or ear canal tissue. The cap 42 preferably is transparent or highly translucent material and preferably is made of 100% food grade silicone.

The bridge member 44 preferably is elongated plastic material. The light-radiation modules are housed within the base 6 of waterproof compartments 56 at each base 6. Since ear and nasal cavities of a person are smaller than the oral cavity, the nasal LED device 70 may contain fewer LEDs than the embodiment designed as a pacifier 10 for oral use shown in FIGS. 1-4. In the nasal LED device 70 and ear LED device 80a, 80b, only one or two LEDs may fit within the compartment 56. When the device 70 is on, light emanating from the LED projects from the LED through the optical guide 38 enclosed by the elongated tubular region 40 of the device 80a, 80b. Light projects out of the device and onto damaged tissue. The elongated tubular region 40 is preferably cylindrical in shape but can be shaped in any manner to direct light emitted from the light radiation module through the silicone cap 42.

When the light contacts wounds in the nasal cavity or ear canal, the wavelength and pulsed frequency of the light increases healing of the wounds as previously described. Preferably, light for nasal cavities healing is around 680 nm, and preferably between approximately 650 nm and 700 nm. Increased healing also occurs when the light is pulsed at the Nogier frequencies. Light therapy using the nasal LED device 70 reduces pain and increases speed of healing of irritated or infected nasal cavities of a person suffering from a cold, sinusitis, or other nasal ailment. Preferably, the light penetration depth is at least between 2 mm-7.5 mm for nasal LED devices 70, which reduces pain and increases the speed of healing of irritated or infected nasal tissue. For embodiments designed to fit the ear canal, use of the devices 80a, 80b reduces pain and increases the speed of healing of ear infections for infants and adults. Ear LED devices 80a, 80b preferably use a wavelength of light between 640 nm to 680 nm and have a light depth penetration of about 1 mm to 7.5 mm.

The dimensions of each of the ear devices 80a, 80b are approximately 1 inch (2.5 cm) in length, 0.75 inches (2.0 cm) in height, and 0.75 inches (2.0 cm) in depth, but other sizes can be made to fit a variety of cavities. In a preferred embodiment, the light power density (irradiance) is approximately 1.75 W/m$^2$.

Figure 7:
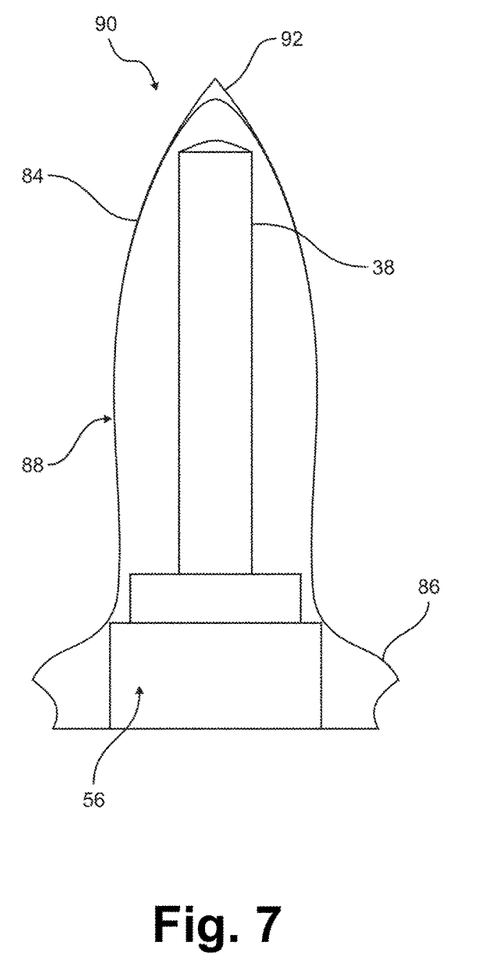
FIG. 7 is a cross sectional view of an embodiment of the device designed for use within the vaginal or anal cavity of a person.
Figure 8:
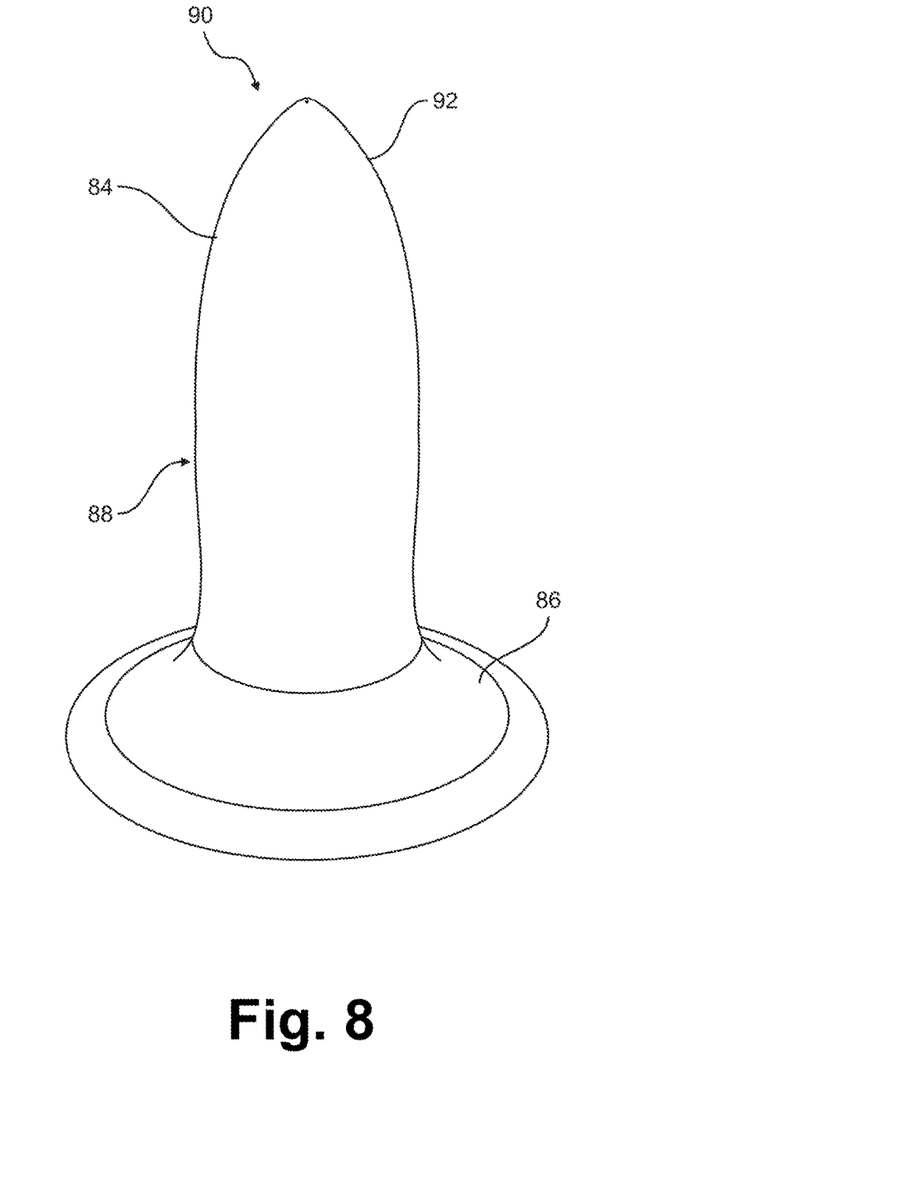
FIG. 8 is a perspective view of the embodiment of FIG. 7.

FIGS. 7-8 illustrate an embodiment of an LED device 90 for use vaginal or anal applications using the same LED internal components described in the previous embodiments. The vaginal LED device 90 has a top region 92, an elongated housing 88, and a base 86. The vaginal LED device 90 can be sized to fit a variety of cavity sizes, but in a preferred embodiment is approximately 2.5 inches long (about 6.4 cm) and 0.5 inches wide (about 1.3 cm). Other embodiments between 1.0-6.0 inches long (2.5 cm to 15 cm) and 0.25-1.0 inches wide (0.6 cm to 2.5 cm) can be envisioned without detracting from the purpose of the device 90. The light power density of the device in a preferred embodiment is approximately 7.5 W/m$^2$.

The elongated housing 88 has an outer transparent or translucent shell 84 and an inner optical guide 38 within the shell 84. The outer shell 84 is preferably made from a soft flexible silicone rubber case having topography to maximize diffusion of light and light scattering of LED light. Mechanisms of diffusing light include surface scattering from roughness and subsurface scattering from irregularities in solids. The optical guide 38 is disposed substantially along the vertical axis of the vaginal device 90 following the direction of the elongated body 88. At least one, but preferably a plurality of LEDs are aligned along or within the optical guide 38 of the device 90 to increase irradiance. The optical guide 38 may be a hollow tubular structure within the device 90 or other structure capable of guiding light along the vertical axis of the device 90. Providing power to the LEDs, as well as electronic control, is a light radiation module 16 (illustrated in FIGS. 1 and 4). The light radiation module 16 and other components are housed within a waterproof compartment 56 at the base 86 of the vaginal LED device 90. When the device 90 is on, light emanates from the LEDs and is guided through the optical guide 38 within the elongated body 88 and scatters in multiple directions out of the device 90 to maximize vaginal or anal surface exposure to the light.

For hygienic purposes, the vaginal LED device 90 may be covered with a one-time use flexible elastomeric sheath, such as a condom (not shown). To increase the effectiveness of the healing, the sheath may be coated with a lubricant ointment or active cream. Light therapy devices that use red LEDs, pulsed at known healing frequencies, in combination with applying tissue healing lotions and ointments, increase the effectiveness of the light therapy devices.

While the invention has been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

What is claimed is:

1. A light-emitting diode (LED) therapy device to target surfaces within a cavity, the device comprising:
   (i) a housing;
   (ii) a light radiation module substantially enclosed within the housing, the light radiation module having,
      (a) an LED for emitting light having at least one predetermined wavelength,
      (b) a controller unit connected to the LED, the controller unit capable of controlling pulse frequency of the LED for at least one predetermined frequency;
      (c) a power source electrically connected to the controller unit;
   (iii) a light diffusing member connected to the housing, the light diffusing member designed to diffuse and project light emitted from the LED; and
   (iv) a safety sensor, the safety sensor capable of deactivating the LEDs when the safety sensor measures light levels below the light levels emitted by the LEDs when contained within an animal cavity.

2. The device of claim 1, and wherein the predetermined wavelength is between 600 nm and 700 nm, and wherein the at least one predetermined frequency is at least one of a Nogier frequency and a harmonic of the Nogier frequency, whereby light pulsed at the Nogier frequency or the harmonic of the Nogier frequency increases the rate of tissue repair compared to the rate of tissue repair when tissue is treated by light not pulsed at the Nogier frequency.

3. The device of claim 2, wherein the Nogier frequency is at least one of 292 Hz, 584 Hz, and 1168 Hz.

4. A light-emitting diode (LED) therapy device comprising a first device of claim 3 and a second device of claim 3,
   wherein the first and the second devices are connected to each other via a bridge member; and,
   wherein the optical guide of the first device and the optical guide of the second device are spaced between 1 and 3 centimeters from each other and designed to fit within two nostrils of a human,
   whereby light emanating from the first and second devices is directed to a nasal cavity of a human.

5. The device of claim 1,
   wherein the predetermined wavelength is between 600 nm and 980 nm, and wherein the at least one predetermined frequency is a predetermined frequency within 30 percent of a Nogier frequency.

6. The device of claim 1,
   wherein the light diffusing member is a flexible silicone nipple having an outer surface, an internal cavity defined by an internal surface, a top region, a middle region, and a base region substantially encircling the LED, wherein the top region of the silicone nipple permits light from the LED to emit from the LED through the internal cavity of the nipple to the top region of the silicone nipple to exit from the top region of the silicone nipple, thereby allowing light form the LED to illuminate an oral cavity of a person when the silicone nipple is placed within the oral cavity;
   wherein the power source is a rechargeable battery.

7. The device of claim 6, wherein the Nogier frequency is at least one of 292 Hz, 584 Hz, and 1168 Hz.

8. The device of claim 1,
   wherein the light radiation module further comprises a Bluetooth module and a wireless charging receiving inductive coil.

9. The device of claim 1, characterized as having an elongated body,
   wherein the housing is an elongated housing comprised of a transparent or translucent silicone rubber;
   wherein the housing encloses an optical guide for placement of a plurality of the LEDs along a longitudinal axis of the device;
   wherein the optical guide is connected to a compartment enclosing the power source; and,
   wherein the power source is a rechargeable power source.

10. The device of claim 9, further comprising an elastomeric tubular sheath designed to fit over the elongated housing and conform to the general shape of the elongated housing.

11. The device of claim 10, wherein the elastomeric tubular sheath is coated with a lubricant to aid in insertion of the device into a cavity.

12. The device of claim 10, wherein the elongated tubular sheath is a latex sheath.

13. The device of claim 10, wherein the housing is characterized has having a base region, the base region having an indentation to secure the tubular sheath to the elongated housing.

14. The device of claim 1, wherein when the safety sensor measures a drop of light intensity, the safety sensor is capable of turning off the LEDs of the device.

15. The device of claim 1, further comprising:
   a mouth shield between the light radiation module and light diffusing member to prevents an infant from inserting the entirety the device into a mouth;
   a light pipe positioned on top of the LED and within an internal cavity of the light diffusing member, the light pipe having a base and a top, the top of the light pipe angled to emit light at a wider angle compared to light emitted by the LED without the light pipe, thereby increasing exposure of LED light to an infant's gums;
   wherein the light pipe comprises an aperture allowing for air to pass from the cavity of the nipple to a waterproof compartment enclosed by the housing, the aperture used for balancing the air pressure between the internal cavity of the light diffusing member and the waterproof compartment; and,
   at least one temperature sensor embedded within or adjacent to the light diffusing member, the at least one temperature sensor adapted to measure a temperature of an infant's gums.

16. The device of claim 1, wherein the housing comprises an optical guide for directing light through the housing, the housing characterized as having an elongated tubular region, the elongated tubular region having a first end in proximity to the LED and a second end opposing the first end;
   wherein the light-diffusing member is flexible silicone cap designed to attach to the second end of the elongated tubular region.

17. The device of claim 16, wherein the removable flexible silicone cap is made from a porous and acoustically permeable material and designed to fit firmly within an ear canal of a human.

18. A method of promoting healing of tissues using red LEDs, comprising:
   inserting a device into an animal cavity, wherein the device includes a housing, a light radiation module substantially enclosed within the housing, an LED having at least one predetermined wavelength, a controller unit connected to the LED, the controller unit capable of controlling pulse frequency of the LED at least one predetermined frequency, a power source, and a light diffusing member connected to the housing;

a safety sensor measuring the light emitted from the LEDs, wherein the safety sensor deactivates the LEDs when the safety sensor measures a drop in the intensity of light levels below that measured by the safety sensor when the safety sensor and the LEDs are inside an animal cavity;

illuminating the LED at a wavelength between 600 nm and 700 nm; and, pulsing the LED at a Nogier frequency.

19. The method of claim 18 where in the Nogier frequency is at least one of 292 Hz, 584 Hz, and 1168 Hz.

20. The method of claim 18, wherein inserting the device is characterized as inserting the device into at least one of a mouth, an ear canal, a nostril, an anal cavity and a vaginal cavity.

* * * * *